United States Patent
Komiya et al.

(10) Patent No.: US 8,870,005 B2
(45) Date of Patent: Oct. 28, 2014

(54) CHEMICAL BOTTLE FOR ENDOSCOPE CLEANING/DISINFECTING APPARATUS

(75) Inventors: Takaaki Komiya, Hachioji (JP); Hisashi Kuroshima, Hachioji (JP); Eiri Suzuki, Sagamihara (JP); Hideto Onishi, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/246,402

(22) Filed: Sep. 27, 2011

(65) Prior Publication Data

US 2012/0125878 A1 May 24, 2012

Related U.S. Application Data

(63) Continuation of application No. PCT/JP2011/063065, filed on Jun. 7, 2011.

(30) Foreign Application Priority Data

Nov. 24, 2010 (JP) .................................. 2010-261090

(51) Int. Cl.
*B65D 1/02* (2006.01)
(52) U.S. Cl.
USPC .......................... 215/379; 215/382; 215/395
(58) Field of Classification Search
CPC . B65D 1/0261; B65D 1/02; B65D 2501/0081
USPC ............ 215/379, 399, DIG. 3, 386, 395, 381, 215/382, 383; 422/292, 300; 220/675
See application file for complete search history.

(56) References Cited

U.S. PATENT DOCUMENTS

| 6,379,632 | B1 | 4/2002 | Kinoshita et al. |
| 6,656,438 | B1 | 12/2003 | Kinoshita et al. |
| 6,962,272 | B2 * | 11/2005 | LeBlond ...................... 222/180 |
| 2007/0193605 | A1 | 8/2007 | Kuroshima et al. |
| 2008/0115814 | A1 | 5/2008 | Hasegawa et al. |
| 2008/0118420 | A1 | 5/2008 | Kotani et al. |

FOREIGN PATENT DOCUMENTS

| EP | 1 025 795 A1 | 8/2000 |
| EP | 1 025 862 A2 | 8/2000 |
| EP | 1 815 782 A2 | 8/2007 |
| JP | 2000-287924 | 10/2000 |
| JP | 2000-288609 | 10/2000 |
| JP | 2003-111725 | 4/2003 |
| JP | 2004-121832 | 4/2004 |
| JP | 2007-202859 | 8/2007 |
| JP | 2010-167284 | 8/2010 |
| WO | WO 2008/059601 A1 | 5/2008 |
| WO | WO 2008/059602 A1 | 5/2008 |

* cited by examiner

*Primary Examiner* — Stephen Castellano
(74) *Attorney, Agent, or Firm* — Scully, Scott, Murphy & Presser, P.C.

(57) ABSTRACT

The present invention includes a storing section that stores a chemical, an opening provided in an upper surface, a concave portion formed in a first side face, and an inclined face that is formed at a face on an upper surface side of the concave portion and that inclines towards the upper surface side. The center of the concave portion is positioned so as to deviate from the central axis at the first side face.

2 Claims, 12 Drawing Sheets

CHEMICAL BOTTLE FOR ENDOSCOPE CLEANING/DISINFECTING APPARATUS

CROSS REFERENCE TO RELATED APPLICATION

This application is a continuation application of PCT/JP2011/063065 filed on Jun. 7, 2011 and claims benefit of Japanese Application No. 2010-261090 filed in Japan on Nov. 24, 2010, the entire contents of which are incorporated herein by this reference.

BACKGROUND OF THE INVENTION

1. Field of the Invention

The present invention relates to a chemical bottle for an endoscope cleaning/disinfecting apparatus that supplies a chemical to an endoscope cleaning/disinfecting apparatus.

2. Description of the Related Art

When a chemical bottle is set in an insertion portion of an endoscope cleaning/disinfecting apparatus by inserting the chemical bottle therein in an inclined manner, a stopper portion that is provided at an upper surface of a storing section of the chemical bottle is opened by being broken by a cutting portion that is positioned at an inner part of the insertion portion. As a result, a chemical that is inside the chemical bottle is filled into a chemical tank of the endoscope cleaning/disinfecting apparatus through a conduit under its own weight. In this connection, for example, a concentrate of a disinfectant solution to be used for disinfecting an endoscope or a buffer solution of the disinfectant solution is filled inside the chemical bottle.

With respect to the process of setting the chemical bottle in the insertion portion, Japanese Patent Application Laid-Open Publication No. 2004-121832 discloses an endoscope cleaning/disinfecting apparatus in which two lever-type limit switches are provided in the insertion portion. According to this configuration, after the chemical bottle is inserted into the insertion portion, a first limit switch detects a position of the chemical bottle immediately before the cutting portion is stuck into the stopper portion, and a second limit switch detects a chemical bottle insertion completion position at which the cutting portion opens the stopper portion of the chemical bottle.

The endoscope cleaning/disinfecting apparatus disclosed in Japanese Patent Application Laid-Open Publication No. 2004-121832 has a configuration such that a contact portion that is provided at a distal end of an arm portion of each lever-type limit switch contacts a side face of the chemical bottle, and a switch state of the relevant limit switch is switched from "off" to "on" as the result of the contact portion being pressed by the chemical bottle.

In this case, a configuration may also be considered in which a concave portion is provided on a side face of a chemical bottle, and in which a position of the chemical bottle is detected by a switch state being switched from "on" to "off" when a state is entered in which a contact portion of a limit switch is not pressed by the chemical bottle as a result of the contact portion being fitted in the concave portion. For example, a configuration may also be considered that detects the aforementioned chemical bottle insertion completion position as a result of a contact portion of a limit switch being fitted in the concave portion.

The present invention has been conceived in view of the above described circumstances, and an object of the present invention is to provide a chemical bottle for an endoscope cleaning/disinfecting apparatus having a configuration which enables easy withdrawal from an insertion portion of an endoscope cleaning/disinfecting apparatus without damaging a limit switch.

SUMMARY OF THE INVENTION

A chemical bottle for an endoscope cleaning/disinfecting apparatus according to one aspect of the present invention is a chemical bottle for an endoscope cleaning/disinfecting apparatus that supplies a chemical to an endoscope cleaning/disinfecting apparatus, that includes: a storing section that stores the chemical and that includes an upper surface, a bottom surface facing the upper surface, a first side face that connects the upper surface and the bottom surface, and a second side face that connects the upper surface and the bottom surface and that faces the first side face; an opening that is provided in the upper surface and whose center is disposed further to a side of the second side face than a center of the upper surface; a concave portion that is formed in the first side face; and an inclined face that is formed in a face on the upper surface side of the concave portion, and that inclines to the upper surface side; wherein, a center of the concave portion is positioned so as to deviate from a central axis along a direction connecting the upper surface and the bottom surface at the first side face.

A chemical bottle for an endoscope cleaning/disinfecting apparatus according to another aspect of the present invention is a chemical bottle for an endoscope cleaning/disinfecting apparatus that supplies a chemical to an endoscope cleaning/disinfecting apparatus, that includes: a storing section that stores the chemical and that includes an upper surface, a bottom surface facing the upper surface, a first side face that connects the upper surface and the bottom surface, and a second side face that connects the upper surface and the bottom surface and that faces the first side face; an opening that is provided in the upper surface and whose center is disposed further to a side of the second side face than a center of the upper surface; and a concave portion that is formed in the first side face; wherein: an area between the concave portion and the upper surface has a configuration that is irreversibly deformed or broken from the bottom surface side towards the upper surface side; and a center of the concave portion is positioned so as to deviate from a central axis along a direction connecting the upper surface and the bottom surface at the first side face.

DETAILED DESCRIPTION OF THE PREFERRED EMBODIMENTS

Embodiments of the present invention are described hereunder with reference to the drawings. It should be noted that the drawings are schematic ones in which the relationship between the thickness and width of each member, the thickness ratios of the members, and the like are different from those of actual members. Naturally, the drawings include portions in which the dimensional relationships and ratios are different from one another.

First Embodiment

Figure 1:
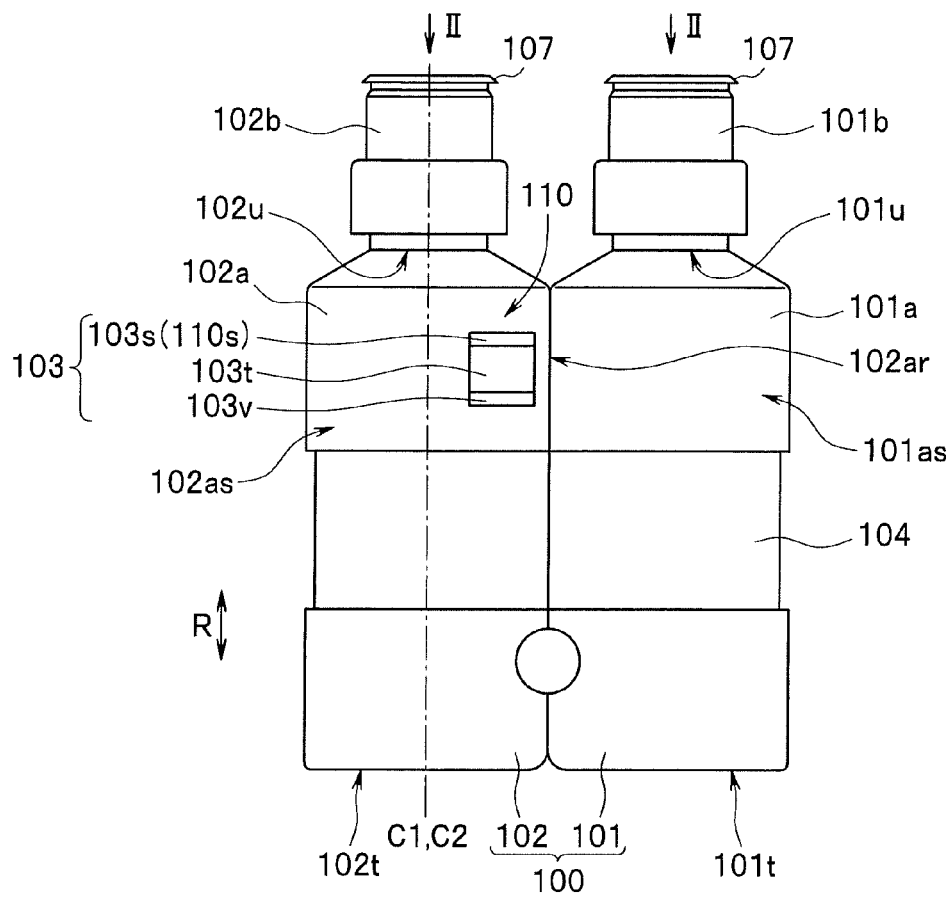
FIG. 1 is a plan view that illustrates chemical bottles for an endoscope cleaning/disinfecting apparatus.
Figure 2:
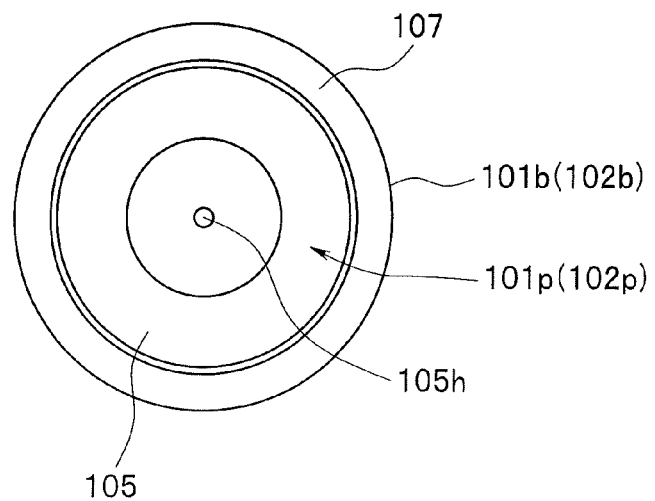
FIG. 2 is an enlarged plan view of a spout portion of a chemical bottle shown in FIG. 1 as viewed from the direction of an arrow II in FIG. 1.
Figure 3:
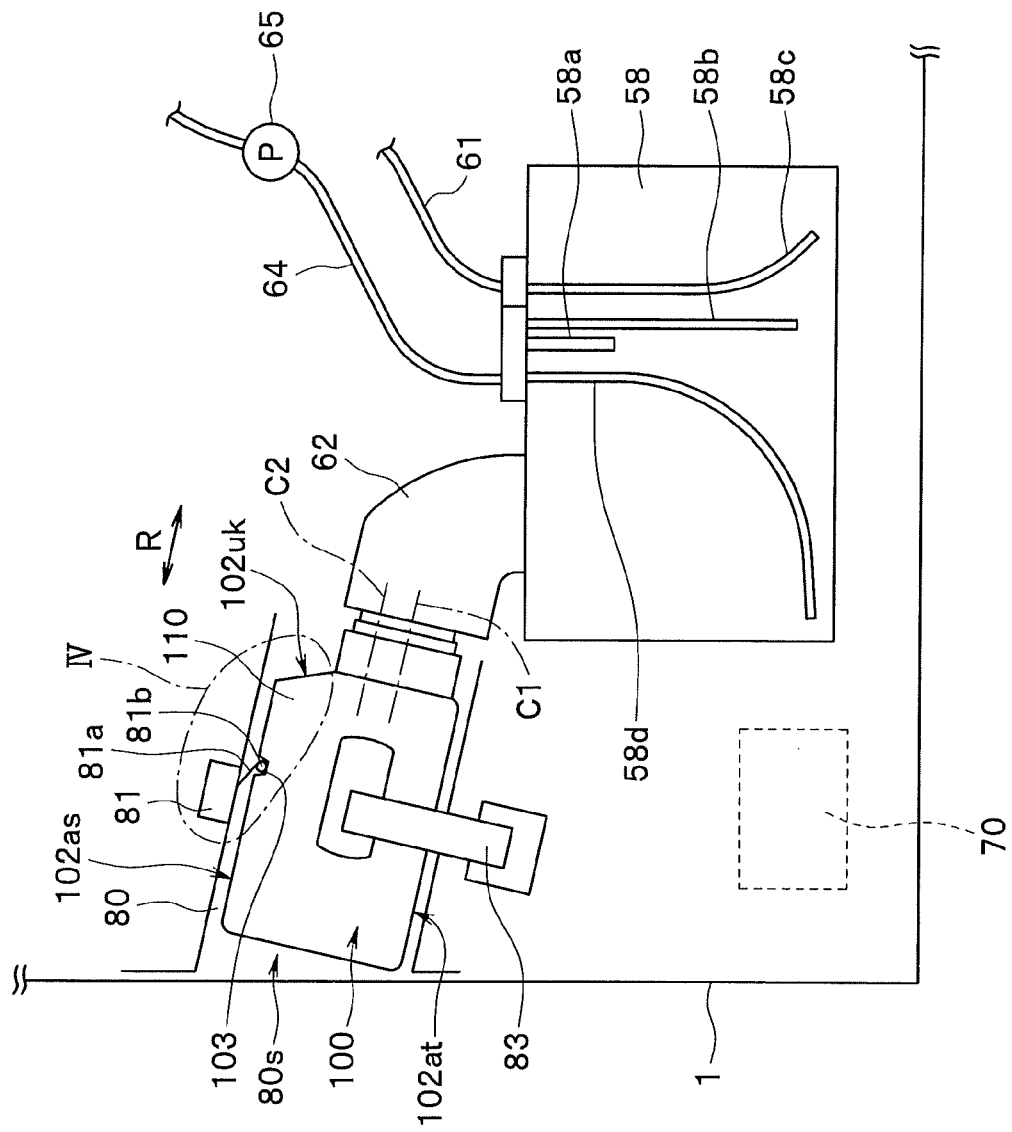
FIG. 3 is a view that illustrates an outline of a configuration for filling a chemical into a chemical tank of an endoscope cleaning/disinfecting apparatus having an insertion portion into which the chemical bottles for an endoscope cleaning/disinfecting apparatus shown in FIG. 1 are inserted.

FIG. 1 is a plan view that illustrates chemical bottles for an endoscope cleaning/disinfecting apparatus. FIG. 2 is an enlarged plan view of a spout portion of a chemical bottle shown in FIG. 1 as viewed from the direction of an arrow II in FIG. 1. FIG. 3 is a view that illustrates an outline of a configuration for filling a chemical into a chemical tank of an endoscope cleaning/disinfecting apparatus having an insertion portion into which the chemical bottles for an endoscope cleaning/disinfecting apparatus shown in FIG. 1 are inserted.

Figure 4:
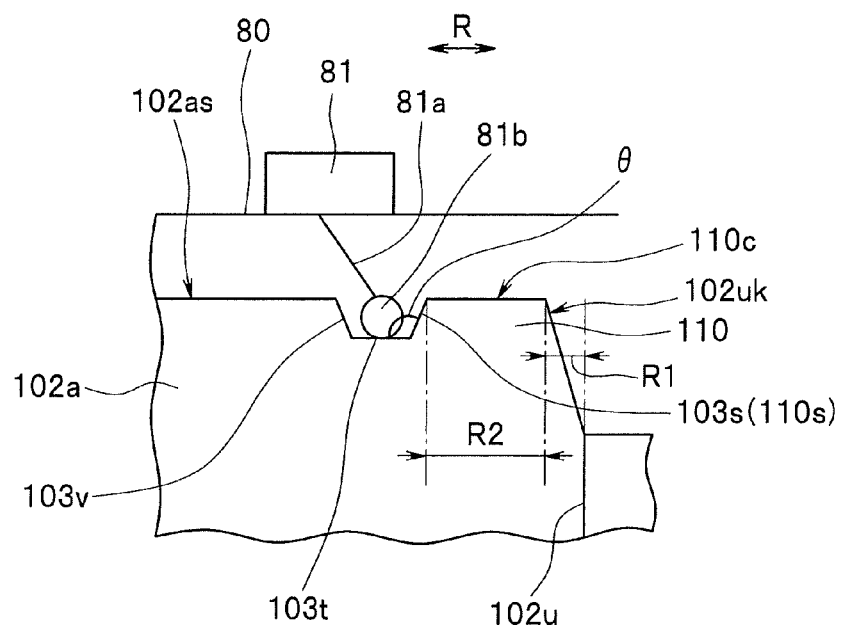
FIG. 4 is a view that illustrates, in an enlarged manner, an area surrounded by an alternate long and short dashed line IV in FIG. 3.
Figure 5:
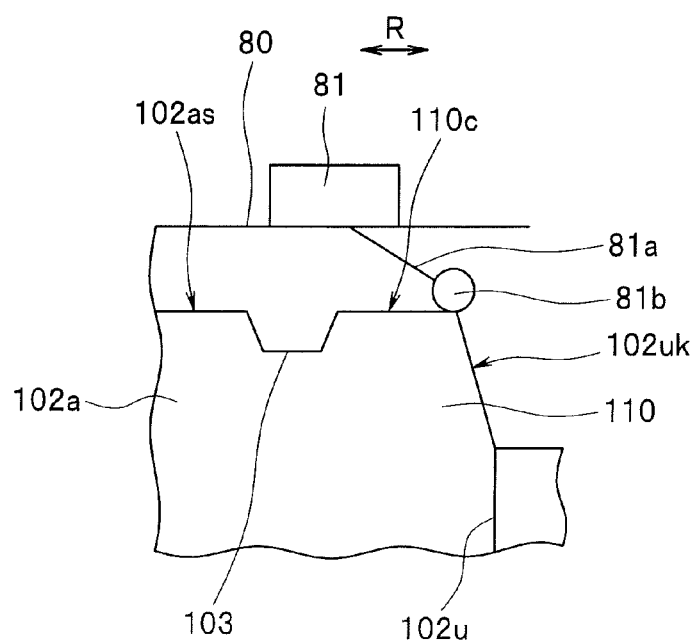
FIG. 5 is a view that schematically shows a state in which a contact portion of a limit switch shown in FIG. 3 contacts a chemical bottle for an endoscope cleaning/disinfecting apparatus such that the contact portion is pressed and a switch state of the limit switch enters an "on" state.

Further, FIG. 4 is a view that illustrates, in an enlarged manner, an area surrounded by an alternate long and short dashed line IV in FIG. 3. FIG. 5 is a view that schematically shows a state in which a contact portion of a limit switch shown in FIG. 3 contacts a chemical bottle for an endoscope cleaning/disinfecting apparatus such that the contact portion is pressed and a switch state of the limit switch enters an "on" state.

As shown in FIG. 1, chemical bottles for an endoscope cleaning/disinfecting apparatus 100 that supplies a chemical to an endoscope cleaning/disinfecting apparatus 1 (see FIG. 3) include, for example, two chemical bottles 101 and 102.

The chemical bottle 101 and chemical bottle 102 are integrally constructed so that positions of bottom surfaces 101t and 102t and of upper surfaces 101u and 102u of the chemical bottles 101 and 102, respectively, match by means of a band-like member 104. Hence, the chemical bottles 101 and 102 are integrally inserted into an insertion portion 80 of the endoscope cleaning/disinfecting apparatus 1 (both are shown in FIG. 3).

In this connection, naturally the chemical bottles for an endoscope cleaning/disinfecting apparatus 100 may be constituted by a single bottle or three or more bottles.

The chemical bottle 101 principally includes a storing section 101a in which a chemical is stored, an opening 101p (see FIG. 2) that is provided in the upper surface 101u of the storing section 101a, a stopper portion 105 that is provided in the opening 101p and that can be broken by an unshown cutting portion of the endoscope cleaning/disinfecting apparatus, and a cylindrical spout portion 101b that is provided so as to surround an outer circumference of the stopper portion 105 at the upper surface 101u of the storing section 101a and also protrude from the upper surface 101u.

For example, a concentrate of a disinfectant solution is stored inside the storing section 101a. Peracetic acid or the like may be mentioned as one example of the disinfectant solution. The diameter of the opening 101p is set to a diameter such that, after insertion into the insertion portion 80 (see FIG. 3) that is described later, a chemical that is stored in the storing section 101a is discharged under its own weight.

As shown in FIG. 3, a central axis C1 of the opening 101p along a connection direction R is positioned further to a side of a side face 101 at (not shown) that faces a side face 101 as, described later, than a central axis C2 of the chemical bottle 101.

A seal portion 107 is provided at an outer circumferential edge portion at a protruding end of the spout portion 101b. When the chemical bottle 101 is inserted in the insertion portion 80 of the endoscope cleaning/disinfecting apparatus 1, the seal portion 107 seals the spout portion 101b with respect to a conduit 62 (see FIG. 3), which is described later, by contacting an inner surface portion of the conduit 62 in a watertight and airtight manner with an elastic force.

The chemical bottle 102 principally includes a storing section 102a in which a chemical is stored, an opening 102p (see FIG. 2) that is provided in the upper surface 102u of the storing section 102a, a stopper portion 105 (see FIG. 2) that is provided in the opening 102p and that can be broken by the aforementioned cutting portion, and a cylindrical spout portion 102b that is provided so as to surround an outer circumference of the stopper portion 105 at the upper surface 102u of the storing section 102a and also protrude from the upper surface 102u.

For example, a buffer solution of a disinfectant solution is stored in the storing section 102a. The buffer solution has a function of increasing a penetration force of the disinfectant solution with respect to an endoscope, and also of making the disinfectant solution last for a longer time. The diameter of the opening 102p is set to a diameter such that, after insertion into the insertion portion 80 (see FIG. 3) that is described later, a chemical stored in the storing section 102a is discharged under its own weight.

As shown in FIG. 3, a central axis C1 of the opening 102p along the connection direction R is positioned further to a side of another side face 102 at that faces a side face 102as, described later, than a central axis C2 of the chemical bottle 101.

A seal portion 107 is provided at an outer circumferential edge portion at a protruding end of the spout portion 102b. When the chemical bottle 102 is inserted in the insertion portion 80 of the endoscope cleaning/disinfecting apparatus 1, the seal portion 107 seals the spout portion 102b with respect to the conduit 62 (see FIG. 3), which is described later, by contacting an inner surface portion of the conduit 62 in a watertight and airtight manner with an elastic force.

Further, among four side faces that connect the upper surface 102u and the bottom surface 102t of the storing section 102a of the chemical bottle 102, a convex portion 110 and a concave portion 103 are provided in the side face 102as on a side that faces a limit switch 81 (see FIG. 3), described later, when the chemical bottle 102 is inserted in the insertion portion 80 (see FIG. 3) that is described later. In this connection, the convex portion 110 is formed by the concave portion 103 being formed in the side face 102as, and a first inclined face 102uk that connects the upper surface 102u and the side face 102as being formed with a first length R1 along the connection direction R between the upper surface 102u and the side face 102as.

As shown in FIG. 4, with respect to the side face 102as, in the connection direction R connecting the upper surface 102u and the bottom surface 102t, the convex portion 110 is provided so as to be a second length R2 in the connection direction R at a position separated by the first length R1 from the upper surface 102u by means of the first inclined face 102uk. Note that a top portion 110c of the convex portion constitutes a part of the side face 102as.

Further, as shown in FIG. 1 and FIG. 4, the concave portion 103 includes, in the connection direction R, a bottom surface 103t, a face 103s on the upper surface 102u side that is a second inclined face, and a face 103v on the bottom surface 102t side, and is provided at a position that is further towards the bottom surface 102t side than the convex portion 110 in the connection direction R.

Furthermore, as shown in FIG. 4, a face 110s on the bottom surface 102t side of the convex portion 110 that is the second inclined face, in other words, the face 103s on the upper surface 102u side of the concave portion 103, is formed in an inclined manner with respect to the upper surface 102u side towards the top portion 110c of the convex portion 110.

More specifically, as shown in FIG. 4, the face 110s (103s) is formed as a linear face that inclines to the upper surface 102u side towards the top portion 110c of the convex portion 110 so that an angle 8 formed between the face 110s (103s) and the bottom surface 103t of the concave portion 103 is an obtuse angle.

Further, at the side face 102as, the convex portion 110 and the concave portion 103 are positioned so as to be further to a side of another side face 102ar that is contiguous with the side face 102as than the central axes C1 and C2 along the connection direction R of the storing section 102a and the opening 102p. Alternatively, the convex portion 110 and the concave portion 103 may be shifted to be positioned on the opposite side across the central axes C1 and C2.

In this connection, among four side faces that connect the upper surface 101u and the bottom surface 101t of the storing section 101a of the chemical bottle 101, the convex portion 110 and the concave portion 103 may also be provided in the side face 101 as that is on a side that faces the limit switch 81 (see FIG. 3), described later, when the chemical bottle 101 is inserted in the insertion portion 80 (see FIG. 3) that is described later. In this case, the limit switch 81 has a configuration that contacts the chemical bottle 101.

The chemical bottle 101 and the chemical bottle 102 are formed with the same size and the same shape, except that the convex portion 110 and the concave portion 103 are formed in the chemical bottle 102. Naturally, the chemical bottle 102 may be formed with a different shape and a different size to the chemical bottle 101.

Further, other than the fact that the chemical bottle 102 includes the convex portion 110 and the concave portion 103, the shape of the chemical bottle 102 may be the same as a conventional chemical bottle. If the chemical bottles for an endoscope cleaning/disinfecting apparatus 100 are constituted by a plurality of bottles, the convex portion 110 and the concave portion 103 may be provided in the side face of the storing section of any one of the bottles or may be provided in a plurality of the bottles.

In this connection, when storing a volatile chemical agent, such as peracetic acid, as shown in FIG. 2, a configuration may be adopted in which a hole portion 105h is formed in the stopper portion 105 so that vapor can be released therefrom.

The chemical bottles for an endoscope cleaning/disinfecting apparatus 100 configured in this manner are inserted into the insertion portion 80 of the endoscope cleaning/disinfecting apparatus 1 shown in FIG. 3.

As shown in FIG. 3, the endoscope cleaning/disinfecting apparatus 1 contains a chemical tank 58 therein. The insertion portion 80 is provided at a position above the chemical tank 58. The chemical bottles for an endoscope cleaning/disinfecting apparatus 100 can be inserted into the insertion portion 80 from the upper surface side.

Note that a configuration may also be adopted in which the chemical bottles for an endoscope cleaning/disinfecting apparatus 100 can be inserted into the insertion portion 80 using an unshown cassette tray that can be drawn out from the endoscope cleaning/disinfecting apparatus 1.

The insertion portion 80 has, at one end, an insertion slot 80s that opens to an outer surface of a front face that a user approaches in the endoscope cleaning/disinfecting apparatus 1. At the other end of the insertion portion 80, the conduit 62 that allows the insertion portion 80 and the chemical tank 58 to communicate is connected.

The insertion portion 80 is provided so as to be inclined downward from the one end side towards the other end side so that a chemical inside the chemical bottles for an endoscope cleaning/disinfecting apparatus 100 that are inserted into the insertion portion 80 can be filled into the chemical tank 58 under its own weight through the conduit 62.

An unshown cutting portion is provided on the inner side on the other end side of the insertion portion 80. The cutting portion opens the aforementioned stopper portion 105 of the chemical bottles for an endoscope cleaning/disinfecting apparatus 100 that have been inserted into the insertion portion 80.

The lever-type limit switch 81 is provided on the upper face of the insertion portion 80. The limit switch 81 has an arm portion 81a and a contact portion 81b provided at a distal end of the arm portion 81a.

Although the insertion portion 80 may include a plurality of limit switches, when one limit switch is provided the structure is simplified and the cost of the endoscope cleaning/disinfecting apparatus 1 can be reduced.

The limit switch 81 is configured so that, when the contact portion 81b contacts the outer surface of the storing section 102a of the chemical bottle 102, the contact portion 81b is pressed and the switch state of the limit switch 81 changes from "off" to "on". The limit switch 81 has a function that transmits a change in the switch state thereof to a control portion 70 (see FIG. 3).

More specifically, the limit switch 81 is constituted by a switch that is configured such that when the contact portion 81b is pressed as a result of contact, the switch state switches to "on", and when pressing of the contact portion 81b ends, the switch state switches to "off". Further, the limit switch 81 has a function that detects a position of the chemical bottles for an endoscope cleaning/disinfecting apparatus 100 by transmitting a change in the switch state to the control portion 70.

However, a limit switch may also be used that enters an "off" state when the contact portion 81b is pressed and enters an "on" state when the pressing ends, or in which an electric current value differs between a time when the contact portion 81b is being pressed and a time when pressing of the contact portion 81b has ended.

The limit switch 81 is provided in the upper face of the insertion portion 80 at a position such that the contact portion 81b of the limit switch 81 can contact the convex portion 110 formed in the side face 102as of the storing section 102a of the chemical bottle 102.

The switch state of the limit switch 81 is "off" in both a state in which the chemical bottles for an endoscope cleaning/disinfecting apparatus 100 are not inserted into the insertion portion 80, and a state immediately after the chemical bottles for an endoscope cleaning/disinfecting apparatus 100 have been inserted into the insertion portion 80 through the insertion slot 80s.

Further, when the chemical bottles for an endoscope cleaning/disinfecting apparatus 100 are inserted as far as a position that is immediately before a position at which the above described cutting portion provided in the insertion portion 80 is stuck into the stopper portion 105, as shown in FIG. 5, the switch state of the limit switch 81 changes from "off" to "on" as a result of the contact portion 81b contacting against the convex portion 110 and being pressed thereby.

More specifically, the limit switch 81 detects a position of the chemical bottles for an endoscope cleaning/disinfecting apparatus 100 immediately before the cutting portion is stuck into the stopper portion 105. In this connection, the detection result is sent to the control portion 70.

Further, at the position immediately before the cutting portion is stuck into the stopper portion 105, the respective seal portions 107 provided at the protruding ends of the spout portions 101b and 102b of the respective chemical bottles 101 and 102 constituting the chemical bottles for an endoscope cleaning/disinfecting apparatus 100 contact against the inner surface of the conduit 62 in a watertight and airtight manner with an elastic force.

Further, at the position immediately before the cutting portion is stuck into the stopper portion 105, after the switch state of the limit switch 81 changes to "on", movement in a withdrawal direction along the connection direction R of the chemical bottles for an endoscope cleaning/disinfecting apparatus 100 is locked by a lock portion 83 that is described later.

When the chemical bottles for an endoscope cleaning/disinfecting apparatus 100 are inserted forward in the connection direction R from the position shown in FIG. 5 and are moved as far as a chemical bottle insertion completion position at which the stopper portion 105 is opened as a result of the aforementioned cutting portion sticking into the stopper portion 105 by a predetermined amount, as shown in FIG. 4, the contact portion 81b passes over the convex portion 110 and is fitted into the concave portion 103. Hence, since pressing of the contact portion 81b by the chemical bottle 102 ends, the switch state of the limit switch 81 changes from "on" to "off".

In other words, the switch state of the limit switch 81 changes from "on" to "off" when the contact portion 81b of the limit switch 81 passes over the convex portion 110 from the upper surface 102u side to the bottom surface 102t side.

As a result, the limit switch 81 detects the insertion completion position of the chemical bottles for an endoscope cleaning/disinfecting apparatus 100. The detection result is sent to the control portion 70.

Further, based on the foregoing, the second length R2 (see FIG. 4) in the connection direction R of the convex portion 110 as described above is set so as to equal a distance that the chemical bottles for an endoscope cleaning/disinfecting apparatus 100 move inside the insertion portion 80 from the above described position immediately before the cutting portion is stuck into the stopper portion 105 to the insertion completion position. Alternatively, the position of the limit switch 81 is set in conformity with the second length R2 of the chemical bottles for an endoscope cleaning/disinfecting apparatus 100.

In addition, when withdrawing the chemical bottles for an endoscope cleaning/disinfecting apparatus 100 from the insertion portion 80 after the chemical has been filled from the chemical bottles for an endoscope cleaning/disinfecting apparatus 100, in a state in which the contact portion 81b of the limit switch 81 is contacting the convex portion 110, the contact portion 81b passes over the convex portion 110 from the bottom surface 102t side to the upper surface 102u side along the face 110s (103s) and the top portion 110c. Hence, when the contact portion 81b is being pressed by the convex portion 110, the switch state of the limit switch 81 changes from "off" to "on", and when the contact portion 81b has passed over the convex portion 110, the switch state of the limit switch 81 changes from "on" to "off".

The endoscope cleaning/disinfecting apparatus 1 has the lock portion 83 that uses a known lock arm that inhibits movement in a withdrawal direction with respect to the insertion portion 80 of the chemical bottles for an endoscope cleaning/disinfecting apparatus 100 after the chemical bottles for an endoscope cleaning/disinfecting apparatus 100 have been inserted into the insertion portion 80 as far as the aforementioned position immediately before the cutting portion is stuck into the stopper portion 105 that is shown in FIG. 5. Note that the configuration is such that even when locked by the lock portion 83, the chemical bottles for an endoscope cleaning/disinfecting apparatus 100 can move forward in the insertion direction.

A plurality of level sensors 58a to 58d that detect, in incremental steps, the fluid volume of a chemical stored in the chemical tank 58 are provided inside the chemical tank 58. Information regarding the detected fluid volume of the chemical is transmitted from each of the level sensors 58a to 58d to the control portion 70 provided inside the endoscope cleaning/disinfecting apparatus 1.

An end portion of a chemical recovery conduit 61 that is used when a chemical inside the above described cleaning/disinfecting tank 4 is recovered into the chemical tank 58, and an end portion of a chemical conduit 64 that is used when supplying a chemical into the cleaning/disinfecting tank 4 from the chemical tank 58 are connected to the chemical tank 58. A chemical pump 65 is interposed in the chemical conduit 64.

Thus, according to the present embodiment, the face 110s on the bottom surface 102t side of the convex portion 110 that is formed on the side face 102as of the storing section 102a of the chemical bottle 102, in other words, the face 103s on the upper surface 102u of the concave portion 103, is formed in an inclining manner with respect to the upper surface 102u side towards the top portion 110c of the convex portion 110 so that an angle 8 formed between the face 103s and the bottom surface 103t of the concave portion 103 is an obtuse angle.

Therefore, when withdrawing the chemical bottles for an endoscope cleaning/disinfecting apparatus 100 from the insertion portion 80 after filling of the chemical into the chemical tank 58 from the chemical bottles for an endoscope cleaning/disinfecting apparatus 100 is completed, although conventionally a case has arisen in which, if the face 110s (103s) is formed as a face that is perpendicular to the bottom surface 103t, the contact portion 81b of the limit switch 81 gets caught at the face 103s and as a result, the arm portion 81a of the limit switch 81 becomes damaged if the user attempts to withdraw the chemical bottles for an endoscope cleaning/disinfecting apparatus 100 using force, according to the configuration of the present embodiment, because the face 110s (103s) is formed in an inclined manner with respect to the upper surface 102u side towards the top portion 110c of the convex portion 110, the contact portion 81b does not get caught at the face 110s (103s).

Further, in the present embodiment, at the side face 102as of the storing section 102a of the chemical bottle 102, the convex portion 110 and the concave portion 103 are positioned further to a side of the other side face 102ar that is contiguous with the side face 102as than the central axes C1 and C2 along the connection direction R of the storing section 102a and the opening 102p.

Therefore, the strength of the side face in which the concave portion is provided of the storing section 102a can be enhanced.

Hence, it is possible to provide the chemical bottles for an endoscope cleaning/disinfecting apparatus 100 that have a configuration that can be easily withdrawn from the insertion portion 80 of the endoscope cleaning/disinfecting apparatus 1 without damaging the limit switch 81.

Figure 6:
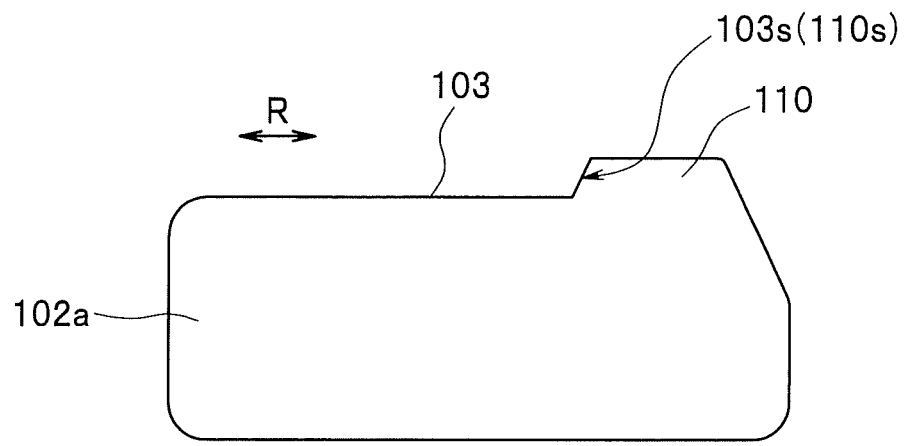
FIG. 6 is a view that illustrates a modification example in which a notch is formed instead of a concave portion that is formed in the chemical bottle for an endoscope cleaning/disinfecting apparatus shown in FIG. 1.

A modification example is described hereunder using FIG. 6. FIG. 6 is a view that illustrates a modification example in which a notch is formed instead of the concave portion that is formed in the chemical bottles for an endoscope cleaning/disinfecting apparatus shown in FIG. 1.

According to the present embodiment described in the foregoing, the convex portion 110 is formed by forming the concave portion 103 in the side face 102as of the storing section 102a of the chemical bottle 102. However, the present invention is not limited thereto, and as shown in FIG. 6, naturally the convex portion 110 may be formed by forming a notch 103 in the side face 102as at an area other than the convex portion 110.

Figure 7:
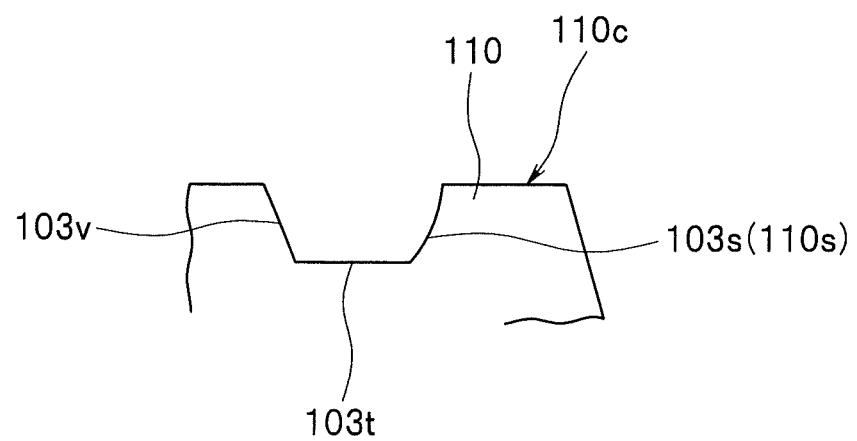
FIG. 7 is a view that illustrates a modification example in which a face on a bottom surface side of a convex portion shown in FIG. 1 is formed as a curved face.
Figure 8:
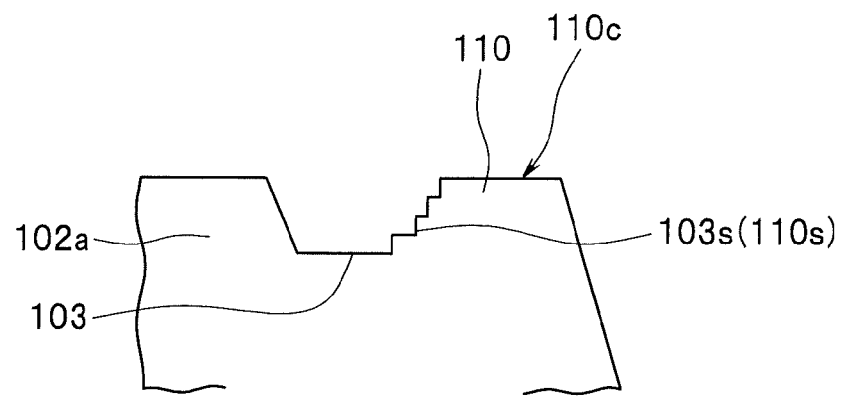
FIG. 8 is a view that illustrates a modification example in which the face on the bottom surface side of the convex portion shown in FIG. 1 is formed as a stepped face.

Another modification example is described hereunder using FIG. 7. FIG. 7 is a view that illustrates a modification example in which a face on a bottom surface side of the convex portion shown in FIG. 1 is formed as a curved face. FIG. 8 is a view that illustrates a modification example in which a face on a bottom surface side of the convex portion shown in FIG. 1 is formed as a stepped face.

According to the present embodiment described in the foregoing, the face 110s on the bottom surface 102t side of the convex portion 110, in other words, the face 103s on the upper surface 102u side of the concave portion 103 is formed in an inclined manner with respect to the upper surface 102u side towards the top portion 110c of the convex portion 110 so that an angle θ formed between the face 103s and the bottom surface 103t of the concave portion 103 is an obtuse angle, and as shown in FIG. 4, the face 110s (103s) is formed as a linear face.

However, the present invention is not limited to the above configuration, and as shown in FIG. 7, the face 110s (103s) is not limited to a linear face as long as the face 110s (103s) is formed in an inclined manner with respect to the upper surface 102u side towards the top portion 110c of the convex portion 110, and the face 110s (103s) may also be formed as a curved face, or as shown in FIG. 8, may be formed as a stepped face.

Thus, even if the face 110s (103s) is formed as a curved face or a stepped face, since the contact portion 81b of the limit switch 81 does not get caught at the face 110s (103s) when withdrawing the chemical bottles for an endoscope cleaning/disinfecting apparatus 100 from the insertion portion 80, a similar effect as in the present embodiment can be obtained.

Note that the shape of the face 110s (103s) is not limited to the above described shapes, and naturally the face 110s (103s) may be of any shape as long as the contact portion 81b of the limit switch 81 does not get caught on the face.

Figure 9:
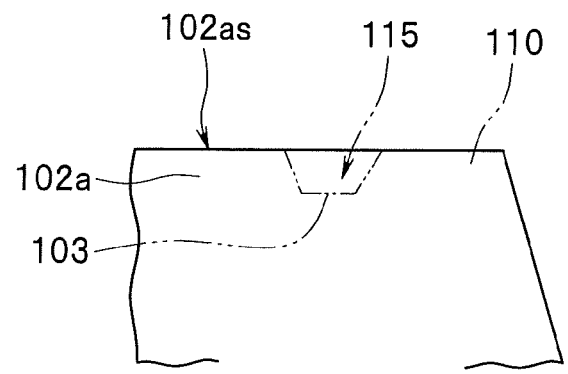
FIG. 9 is a view that illustrates a modification example in which the concave portion shown in FIG. 1 is formed after a deformation portion of a side face of a storing section of the chemical bottle for an endoscope cleaning/disinfecting apparatus has been irreversibly or reversibly deformed.

A still further modification example is illustrated using the FIG. 9. FIG. 9 is a view that illustrates a modification example in which the concave portion shown in FIG. 1 is formed after a deformation portion of a side face of the storing section of the chemical bottle for an endoscope cleaning/disinfecting apparatus has been irreversibly or reversibly deformed.

As shown in FIG. 9, a deformation portion 115 is provided in one part of the side face 102as of the storing section 102a of the chemical bottle 102. The concave portion 103 is formed by the deformation portion 115 being irreversibly or reversibly deformed by contact with the contact portion 81b of the limit switch 81. More specifically, a configuration may be adopted in which the face 110s (103s) that is a second inclined face is formed after formation of the concave portion 103.

In this connection, the deformation portion 115 is constituted by a member with a weak mechanical strength compared to another area of the side face 102as. More specifically, a part of the side face 102as of the storing section 102a is constituted by a thin walled portion that is irreversibly deformed due to a thickness of a member constituting the storing section 102a being thinner than another area, or by a member capable of reversibly deforming, such as rubber, or by a member capable of irreversibly deforming that is different to the storing section 102a or the like.

Figure 10:
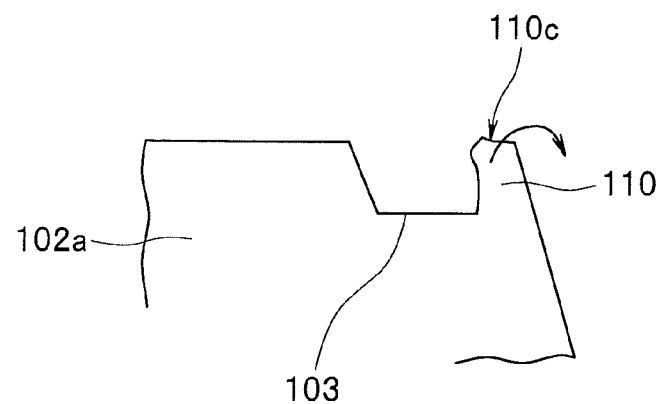
FIG. 10 is a view that illustrates a modification example in which the convex portion shown in FIG. 1 is constituted by a member that is irreversibly deformed or broken from the bottom surface side to an upper surface side of the chemical bottle for an endoscope cleaning/disinfecting apparatus.

A further modification example is described hereunder using FIG. 10. FIG. 10 is a view that illustrates a modification example in which the convex portion shown in FIG. 1 is constituted by a member that is irreversibly deformed or broken from a bottom surface side of the chemical bottles for an endoscope cleaning/disinfecting apparatus to the upper surface side.

As shown in FIG. 10, the convex portion 110 formed in the side face 102as of the storing section 102a may also be constituted by a member that is irreversibly deformed or broken from the bottom surface 102t side to the upper surface 102u side of the chemical bottle 102.

Thus, when withdrawing the chemical bottles for an endoscope cleaning/disinfecting apparatus 100 from the insertion portion 80, since the convex portion 110 deforms or is broken if the contact portion 81b of the limit switch 81 gets caught at the face 110s (103s), the contact portion 81b of the limit switch 81 does not get caught at the face 110s (103s). Hence, a similar effect as the present embodiment can be obtained.

Figure 11:
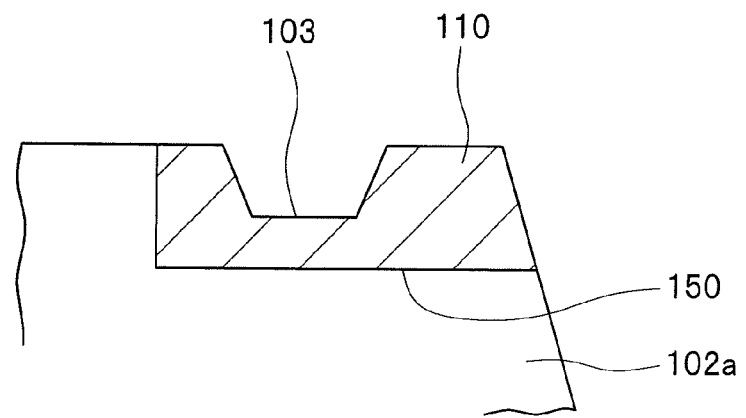
FIG. 11 is a view that illustrates a modification example in which a convex portion and a concave portion that are formed at a side face of the storing section of the chemical bottle for an endoscope cleaning/disinfecting apparatus shown in FIG. 1 are provided in an adapter that is detachable with respect to the side face.
Figure 12:
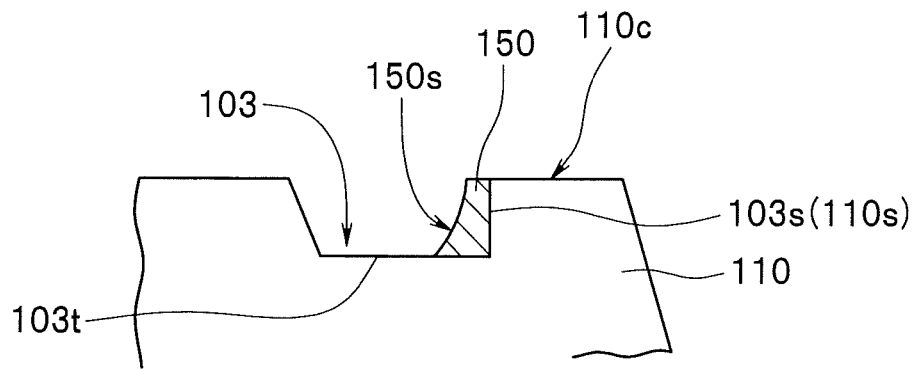
FIG. 12 is a view that illustrates a modification example in which an adapter is detachable with respect to a face on a bottom surface side of a convex portion that is formed in a side face of the storing section of a chemical bottle for an endoscope cleaning/disinfecting apparatus.

A further modification example is described hereunder using FIG. 11 to FIG. 14. FIG. 11 is a view that illustrates a modification example in which the convex portion and the concave portion that are formed in the side face of the storing section of the chemical bottle for an endoscope cleaning/disinfecting apparatus shown in FIG. 1 are provided in an adapter that is detachable with respect to the side face. FIG. 12 is a view that illustrates a modification example in which an adapter is detachable with respect to a face on a bottom surface side of a convex portion that is formed in the side face of the storing section of the chemical bottle for an endoscope cleaning/disinfecting apparatus.

Figure 13:
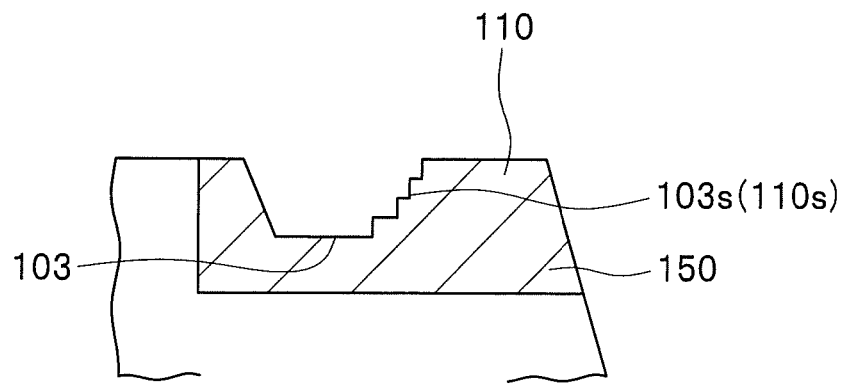
FIG. 13 is a view that illustrates a modification example in which the convex portion and concave portion shown in FIG. 8 that are formed at a side face of the storing section of the chemical bottle for an endoscope cleaning/disinfecting apparatus shown in FIG. 1 are provided in an adapter that is detachable with respect to the side face.

FIG. 13 is a view that illustrates a modification example in which the convex portion and the concave portion shown in FIG. 8 that are formed in the side face of the storing section of the chemical bottle for an endoscope cleaning/disinfecting apparatus shown in FIG. 1 are provided in an adapter that is detachable with respect to the side face.

Figure 14:
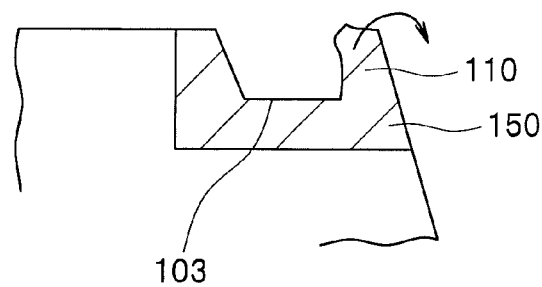
FIG. 14 is a view that illustrates a modification example in which the convex portion and concave portion shown in FIG. 10 that are formed at a side face of the storing section of the chemical bottle for an endoscope cleaning/disinfecting apparatus shown in FIG. 1 are provided in an adapter that is detachable with respect to the side face.

Further, FIG. 14 is a view that illustrates a modification example in which the convex portion and the concave portion shown in FIG. 10 that are formed in the side face of the storing section of the chemical bottle for an endoscope cleaning/disinfecting apparatus shown in FIG. 1 are provided in an adapter that is detachable with respect to the side face.

According to the present embodiment as described above, the convex portion 110 and the concave portion 103 are formed in the side face 102as of the storing section 102a of the chemical bottle 102. However, the present invention is not limited thereto, and as shown in FIG. 11, without providing the convex portion 110 and the concave portion 103 in the side face 102as itself, a configuration may be adopted in which, by making an adapter 150 in which the convex portion 110 and the concave portion 103 are formed detachable with respect to the side face 102as, the convex portion 110 and the concave portion 103 are provided in the side face 102as after mounting the adapter 150 onto the side face 102as.

Further, the adapter 150 is not limited to an adapter having the convex portion 110 and the concave portion 103. For example, as shown in FIG. 12, in a case where the face 110s (103s) on the bottom surface 102t side of the convex portion 110 is formed perpendicularly with respect to a bottom surface 130t of the concave portion 103, the adapter may be an adapter with a curved face 150s that is detachable with respect to the face 110s (103s).

According to the configuration shown in FIG. 12, even when the face 110s (103s) of the convex portion is formed perpendicularly with respect to the bottom surface 130t, the curved face 150s can be provided at the face 110s (103s) by merely mounting the adapter 150 to the face 110s (103s). Hence, a similar effect as that of the present embodiment that is described above can be obtained.

Note that an adapter that is detachable with respect to the face 110s (103s) is not limited to the curved face 150s, and may have a face of any shape as long as the face is one at which the contact portion 81b of the limit switch 81 does not get caught, such as an inclined face that inclined to the top portion 150c side or a stepped face.

Further, as shown in FIG. 13, the adapter 150 may be an adapter in which the face 110s (103s) on the bottom surface 102t side of the convex portion 110 is formed as a stepped face as shown in FIG. 8 that is described above. Further, as shown in FIG. 14, the adapter 150 may be an adapter in which the convex portion 110 is configured to irreversibly change shape or break from the bottom surface 102t side of the chemical bottle 102 to the upper surface 102u side as shown in FIG. 10 that is described above.

Note that the shape of the face 110s (103s) of the adapter 150 is not limited to the above described shapes, and naturally the face may be any shape as long as the face is one at which the contact portion 81b of the limit switch 81 does not get caught.

Second Embodiment

Figure 15:
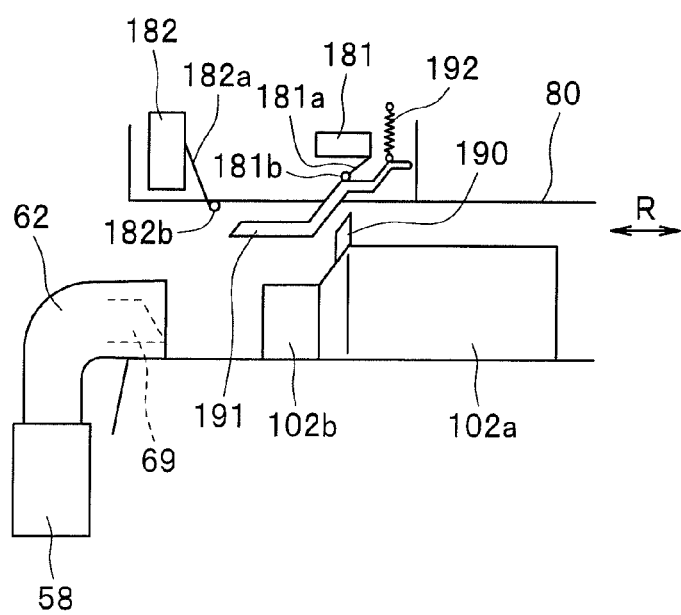
FIG. 15 is a view that schematically shows a state in which insertion of a chemical bottle for an endoscope cleaning/disinfecting apparatus into an insertion portion of an endoscope cleaning/disinfecting apparatus has started.
Figure 16:
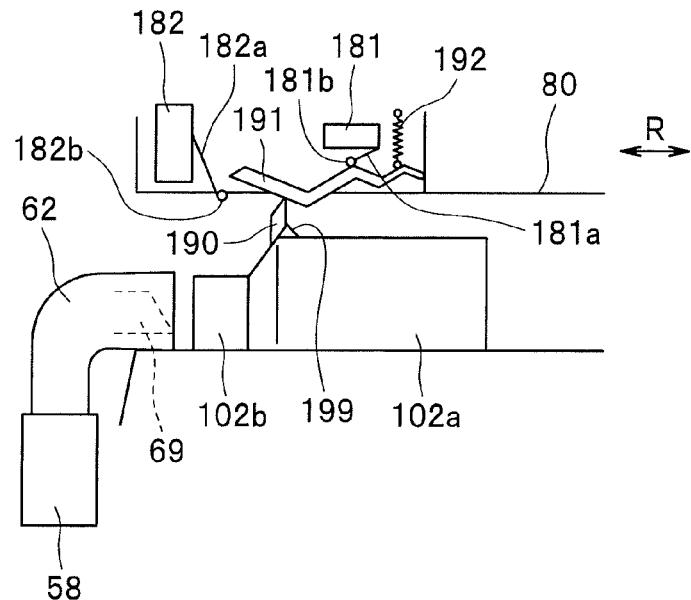
FIG. 16 is a view that schematically shows a state in which a first limit switch provided in the insertion portion shown in FIG. 15 detects the chemical bottle for an endoscope cleaning/disinfecting apparatus.

FIG. 15 is a view that schematically shows a state in which insertion of a chemical bottle for an endoscope cleaning/disinfecting apparatus into an insertion portion of an endoscope cleaning/disinfecting apparatus has started. FIG. 16 is a view that schematically shows a state in which a first limit switch provided in the insertion portion shown in FIG. 15 detects the chemical bottle for an endoscope cleaning/disinfecting apparatus.

Figure 17:
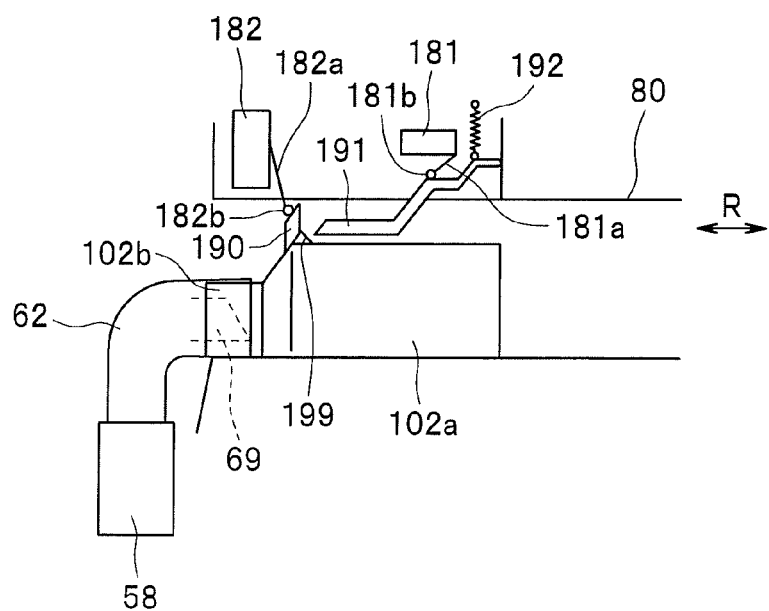
FIG. 17 is a view that schematically shows a state in which a second limit switch provided in the insertion portion shown in FIG. 15 detects the chemical bottle for an endoscope cleaning/disinfecting apparatus.
Figure 18:
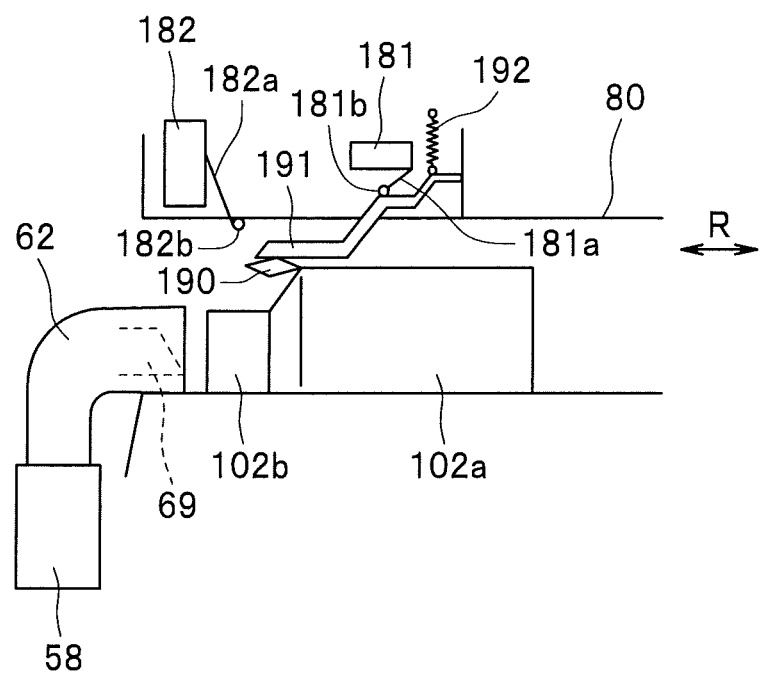
FIG. 18 is a view that schematically shows a state in which, when withdrawing the chemical bottle for an endoscope cleaning/disinfecting apparatus from the state shown in FIG. 17, a connection portion that is connected to a convex portion is broken by a guide plate of the first limit switch.

FIG. 17 is a view that schematically shows a state in which a second limit switch provided in the insertion portion shown in FIG. 15 detects the chemical bottle for an endoscope cleaning/disinfecting apparatus. FIG. 18 is a view that schematically shows a state in which, when withdrawing the chemical bottle for an endoscope cleaning/disinfecting apparatus from the state shown in FIG. 17, a connection portion that is connected to a convex portion is broken by a guide plate of the first limit switch.

In comparison with the chemical bottles for an endoscope cleaning/disinfecting apparatus according to the first embodiment shown in FIG. 1 to FIG. 5 that are described above, the configuration of the chemical bottles for an endoscope cleaning/disinfecting apparatus of the second embodiment differs in that a convex portion is connected through a connection portion to a chemical bottle. Hence, hereunder, only this point of difference is described, and components that are the same as those in the first embodiment are denoted by the same reference symbols and a description of such components is omitted.

According to the present embodiment, an example is described in which two limit switches are provided in the insertion portion 80 of the endoscope cleaning/disinfecting apparatus 1. Further, although the insertion portion 80 appears horizontal in FIG. 15 to FIG. 18 to simplify the illustration in the drawings, in fact the insertion portion 80 is inclined towards the conduit 62 side from the insertion slot 80s, similarly to the first embodiment.

As shown in FIG. 15, two limit switches, namely, a first limit switch 181 and a second limit switch 182, are provided on the upper surface of the insertion portion 80 of the endoscope cleaning/disinfecting apparatus 1.

The first limit switch 181 has a guide plate 191 that is urged towards the inside of the insertion portion 80 by a pressurized spring 192. When the guide plate 191 is pressed, a contact portion 181b provided at a distal end of an arm portion 181a is pressed by the guide plate 191 and thus the switch state of the first limit switch 181 changes.

The second limit switch 182 includes an arm portion 182a and a contact portion 182b. The switch state of the second limit switch 182 changes when the contact portion 182b is pressed.

The chemical bottles for an endoscope cleaning/disinfecting apparatus 100 are inserted into the insertion portion 80 in which the two limit switches 181 and 182 are provided in this manner.

In this connection, the chemical bottles for an endoscope cleaning/disinfecting apparatus 100 according to the present embodiment differ from the first embodiment in the respect that a protruding portion 190 constituting a convex portion is provided through a connection portion 199 to the side face 102as of the storing section 102a of the chemical bottle 102.

The protruding portion 190 is detected by means of the first limit switch 181 and the second limit switch 182. The protruding portion 190 may be integrally provided to the storing section 102a, or may be provided as a separate member thereto. Further, the protruding portion 190 may be provided on the side face 101 as of the storing section 101a of the chemical bottle 101.

The connection portion 199 is constituted by a member that is irreversibly broken from the bottom surface 102t side of the chemical bottle 102 towards the upper surface 102u side thereof. In this connection, the connection portion 199 may also be constituted by a member that is irreversibly deformed from the bottom surface 102t side of the chemical bottle 102 towards the upper surface 102u side thereof.

Thus, when inserting the chemical bottle 102 on which the protruding portion 190 is provided into the insertion portion 80, first, as shown in FIG. 15, the chemical bottles for an endoscope cleaning/disinfecting apparatus 100 are inserted through an unshown insertion slot 80s.

Thereafter, when the chemical bottles for an endoscope cleaning/disinfecting apparatus 100 are inserted further to a cutting portion 69 side than the position shown in FIG. 15, as shown in FIG. 16, the protruding portion 190 pushes up the guide plate 191 against the urging force of the pressurized spring 192.

As a result, the contact portion 181b is pressed and the switch state of the limit switch 181 changes from "off" to "on". Thus, the limit switch 181 detects that the chemical bottles for an endoscope cleaning/disinfecting apparatus 100 are in the process of being inserted.

Subsequently, when the chemical bottles for an endoscope cleaning/disinfecting apparatus 100 are inserted further to the cutting portion 69 side than the position shown in FIG. 16, as shown in FIG. 17, the chemical bottles for an endoscope cleaning/disinfecting apparatus 100 move as far as the insertion completion position at which the stopper portion 105 of each of the chemical bottles 101 and 102 is opened by the cutting portion 69.

At the insertion completion position, since the switch state of the second limit switch 182 changes from "off" to "on" as a result of the contact portion 182b being pressed by the protruding portion 190, the second limit switch 182 detects that the chemical bottles for an endoscope cleaning/disinfecting apparatus 100 are at the insertion completion position.

Finally, after filling of the chemical from the chemical bottles for an endoscope cleaning/disinfecting apparatus 100 to the chemical tank 58 is completed, the chemical bottles for an endoscope cleaning/disinfecting apparatus 100 are withdrawn from the insertion portion 80. In this withdrawing process, as shown in FIG. 18, the connection portion 199 is broken as a result of the protruding portion 190 being caught by the guide plate 191. As a result, the protruding portion 190 collapses to the spout portion 102b side of the chemical bottle 102. At this time, a configuration in which the protruding portion 190 does not separate from the chemical bottle 102 is desirable since the protruding portion 190 does not remain inside the endoscope cleaning/disinfecting apparatus 1.

Therefore, according to the present embodiment, when withdrawing the chemical bottles for an endoscope cleaning/disinfecting apparatus 100 from the insertion portion 80, as the result of being caught on the guide plate 191, the protruding portion 190 that is provided through the connection portion 199 on the side face 102as of the storing section 102a of the chemical bottle 102 collapses to the spout portion 102b side because the connection portion 199 is broken.

Thus, when withdrawing the chemical bottles for an endoscope cleaning/disinfecting apparatus 100 from the insertion portion 80, after the protruding portion 190 collapses, the chemical bottles for an endoscope cleaning/disinfecting apparatus 100 can be easily withdrawn from the insertion portion 80. Hence, it is possible to provide the chemical bottles for an endoscope cleaning/disinfecting apparatus 100 having a configuration that can be easily withdrawn from the insertion portion 80 of the endoscope cleaning/disinfecting apparatus 1 without damaging the limit switch 181.

Further, even if the chemical bottle 102 on which the protruding portion 190 has collapsed is inserted again into the insertion portion 80, since the first limit switch 181 and the second limit switch 182 are not pressed by the collapsed protruding portion 190, the first limit switch 181 and the second limit switch 182 do not enter an "on" state.

In this connection, even if a case is supposed in which the protruding portion 190 is intentionally raised and inserted into the insertion portion 80 in a raised state, since the connection portion 199 is broken, the protruding portion 190 will not press the guide plate 191. Conversely, the protruding portion 190 will be pressed by the guide plate 191 and will collapse again to the spout portion 102 side, and hence the first limit switch 181 will not enter an "on" state.

Therefore, even if a case arises in which an empty chemical bottle that has been used once or a chemical bottle that can no longer be used in which only one of two chemicals remains due to some defect is mistakenly inserted into the insertion portion 80, the endoscope cleaning/disinfecting apparatus 1 immediately shows an error display, and thus the worker can immediately recognize that an incorrect chemical bottle has been inserted. Further, even if the incorrect chemical bottle has been inserted, the endoscope cleaning/disinfecting apparatus 1 can be safely stopped.

Note that the above described embodiments and modification examples can be appropriately combined and used. For example, the concave portion 103 shown in FIG. 6 and the curved face shown in FIG. 7 can be applied to a single bottle. As another example, a bottle on which the protruding portion 190 is provided instead of the convex portion 110 can also be applied to the insertion portion shown in FIG. 3. The combinations are not limited to these examples.

Figure 19:
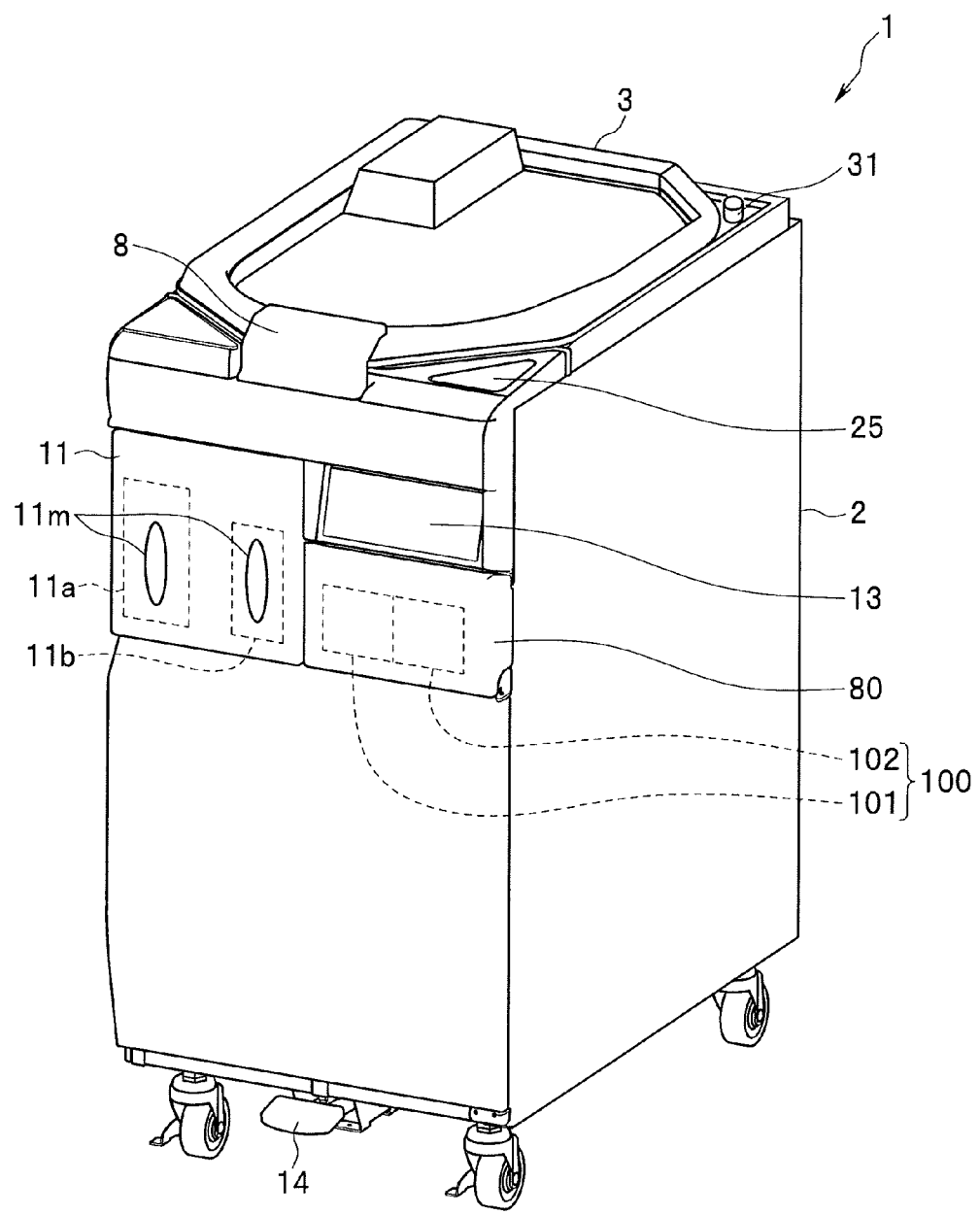
FIG. 19 is a perspective view that illustrates an example of the outer appearance of an endoscope cleaning/disinfecting apparatus.
Figure 20:
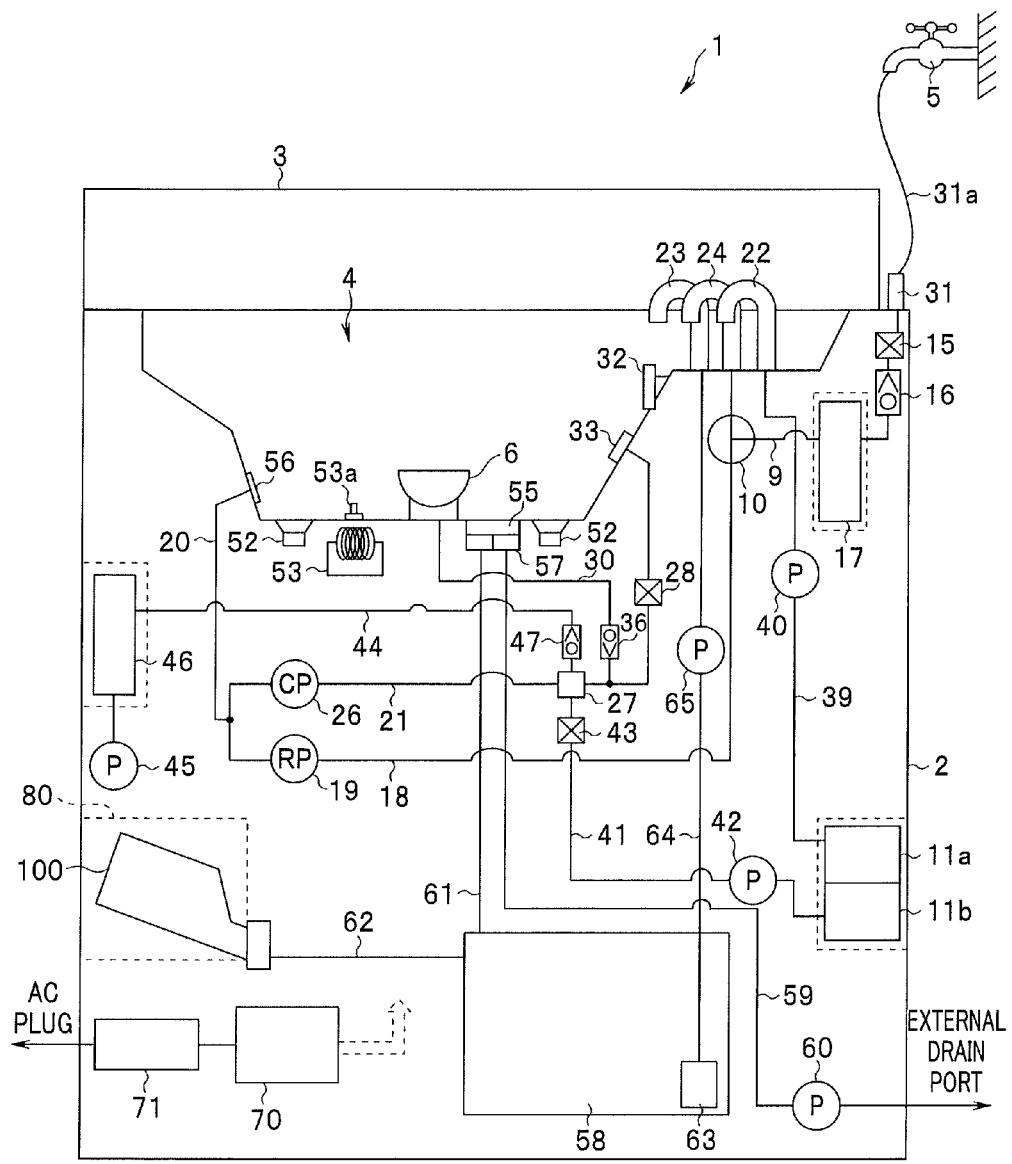
FIG. 20 is a view that illustrates an example of the internal configuration of an endoscope cleaning/disinfecting apparatus.

Hereunder, an example of the configuration of an endoscope cleaning/disinfecting apparatus having the insertion portion 80 into which the chemical bottles for an endoscope cleaning/disinfecting apparatus 100 according to the first and second embodiments are inserted is described using FIG. 19 and FIG. 20. FIG. 19 is a perspective view that illustrates the external appearance of an endoscope cleaning/disinfecting apparatus. FIG. 20 is a view that illustrates an example of the internal configuration of the endoscope cleaning/disinfecting apparatus.

As shown in FIG. 19, an endoscope cleaning/disinfecting apparatus 1 includes, as principal parts, an apparatus body 2 and, on a top portion thereof, a top cover 3. The top cover 3 is connected in an openable/closeable manner to the apparatus body 2 through, for example, an unshown hinge.

In a state in which the top cover 3 is closed on the apparatus body 2, the apparatus body 2 and the top cover 3 are fixed together by, for example, a latch 8 that is arranged at a position facing both the apparatus body 2 and the top cover 3.

A detergent/alcohol tray 11 is arranged at an upper part of a left half portion in FIG. 19, which is the front face in FIG. 19, to which an operator of the apparatus body 2 approaches. The detergent/alcohol tray 11 can be drawn out to the front of the apparatus body 2.

A detergent tank 11a and an alcohol tank 11b are housed in the detergent/alcohol tray 11. The detergent tank 11a stores a detergent that is used when cleaning an endoscope. The alcohol tank 11b stores alcohol that is used when drying an endoscope after cleaning and disinfecting. Since the detergent/alcohol tray 11 can be drawn out to the front of the apparatus body 2, it is possible to fill predetermined liquids into the tanks 11a and 11b.

Two window portions 11m are provided in the detergent/alcohol tray 11. The operator can check the remaining amounts of detergent and alcohol that are stored in the tanks 11a and 11b, respectively, by means of the window portions 11m. The detergent is a concentrated detergent that is to be diluted to a predetermined concentration with tap water after the tap water has been filtered by an unshown water supply filter.

Further, the above described insertion portion 80 is provided at the front of the apparatus body 2 at an upper part of a right half portion in FIG. 19. The above described chemical bottles 101 and 102 can be inserted into the insertion portion 80.

In addition, a sub operation panel 13 is arranged above the insertion portion 80 at the front of the apparatus body 2. The sub operation panel 13 includes a display for displaying a cleaning/disinfecting time and an instruction button for heating a disinfectant solution and the like.

A pedal switch 14 is arranged at the lower part of the apparatus body 2. When the operator depresses the pedal switch 14, the pedal switch 14 opens the top cover 3 that is closed at the upper part of the apparatus body 2 so that the top cover 3 opens in the upward direction from the apparatus body 2.

Further, a main operation panel 25 is provided on the upper face of the apparatus body 2, for example, adjacent to an end portion on the front face side that the operator approaches. The main operation panel 25 includes setting switches for entering settings with respect to the apparatus body 2 such as a cleaning/disinfecting operation start switch and a cleaning/disinfecting mode selection switch.

Further, a water supply hose connection port 31 is arranged on the top face of the apparatus body 2 at a position on a back face side that is opposite to the front face to which the operator approaches. A water supply hose that is connected to a water tap (the water supply hose and water tap are not shown in the drawings) for supplying tap water to the apparatus body 2 is connected to the water supply hose connection port 31. In this connection, a mesh filter for filtering tap water may be disposed on the water supply hose connection port 31.

Hence, as shown in FIG. 20, the endoscope cleaning/disinfecting apparatus 1 has a configuration such that tap water can be supplied thereto by connecting one end of a water supply hose 31a to the water supply hose connection port 31 of the endoscope cleaning/disinfecting apparatus 1, and connecting the other end of the water supply hose 31a to an external water tap 5.

As shown in FIG. 20, the water supply hose connection port 31 is connected to one end of a water supply conduit 9. The other end of the water supply conduit 9 is connected to a three-way electromagnetic valve 10. A water supply electromagnetic valve 15, a check valve 16, and a water supply filter 17 are interposed in the water supply conduit 9 in that order from the side of the water supply hose connection port 31.

The water supply filter 17 is configured as a cartridge-type filter, so that the filter can be periodically replaced. The water supply filter 17 removes contaminants and bacteria and the like in tap water that passes through the water supply filter 17.

The three-way electromagnetic valve 10 is connected to one end of a fluid flow conduit 18, and switches communication of the water supply conduit 9 and the fluid flow conduit 18 with respect to a water supply circulation nozzle 24 by means of an internal valve. That is, the water supply circulation nozzle 24 communicates with either one of the water supply conduit 9 and the fluid flow conduit 18 by the switching operation of the three-way electromagnetic valve 10. Further, a fluid flow pump 19 that is a non-self-priming pump that has excellent liquid transferring performance and that can transfer only a liquid is interposed at the other end side of the fluid flow conduit 18.

One end of a circulation conduit 20 is connected to a circulation port 56 arranged in the cleaning/disinfecting tank 4. The other end of the circulation conduit 20 branches into two so as to communicate with the other end of the fluid flow conduit 18 and one end of a channel conduit 21. The other end of the channel conduit 21 communicates with each air and water supply/forceps port 33. Further, although not shown in the drawings, the other end of the channel conduit 21 also communicates with an unshown forceps raising port.

Partway along the channel conduit 21, a channel pump 26, a channel block 27, and a channel electromagnetic valve 28 are interposed in that order from the one end side thereof. Another end of a case conduit 30 that has one end connected to a cleaning case 6 is connected to the channel conduit 21 between the channel block 27 and the channel electromagnetic valve 28. A relief valve 36 is interposed in the case conduit 30. The channel pump 26 is constituted by a self-priming pump that can transfer both a liquid and a gas at a higher pressure than a non-self-priming pump.

A detergent nozzle 22 is connected to one end of a detergent conduit 39. The other end of the detergent conduit 39 is connected to the detergent tank 11a. A detergent pump 40 constituted by a high-pressure self-priming pump for lifting detergent from the detergent tank 11a to the cleaning/disinfecting tank 4 is provided partway along the detergent conduit 39.

The alcohol tank 11b is connected to one end of an alcohol conduit 41. The alcohol conduit 41 is connected to the channel block 27 so as to communicate with the channel conduit 21 in a predetermined state.

An alcohol supply pump 42 constituted by a high-pressure self-priming pump for lifting alcohol from the alcohol tank 11b to the cleaning/disinfecting tank 4, and an electromagnetic valve 43 are interposed in the alcohol conduit 41.

One end of an air conduit 44 for supplying air from an air pump 45 constituted by a self-priming pump that can transfer a gas is connected to the channel block 27 so as to communicate with the channel conduit 21 in a predetermined state. The other end of the air conduit 44 is connected to the air pump 45. A check valve 47 and an air filter 46 that is periodically exchanged are interposed at positions partway along the air conduit 44.

A switching valve 57 that is capable of being opened and closed is provided in a first drain outlet 55 of the cleaning/disinfecting tank 4. By a switching operation of the switching valve 57, a cleaning solution in the cleaning/disinfecting tank 4 can be drained to the outside of the apparatus or a disinfectant solution can be recovered from the cleaning/disinfecting tank 4 to the chemical tank 58.

The switching valve 57 is connected to one end of a drainage conduit 59 whose other end is connected to and communicates with an unshown drain hose that is connected to an external drain outlet. A drain pump 60 constituted by a non-self-priming pump is interposed in the drainage conduit 59. The switching valve 57 is also connected to one end of a chemical recovery conduit 61. The other end of the chemical recovery conduit 61 is connected to the chemical tank 58.

The chemical tank 58 is also connected to one end of a chemical supply conduit 62 so that, as described above, a chemical, for example, a disinfectant solution, may be supplied thereto from the chemical bottles for an endoscope cleaning/disinfecting apparatus 100. The other end of the chemical supply conduit 62 is connected to a cassette tray 12 in a predetermined state.

One end portion of the chemical conduit 64 is housed in a predetermined state inside the chemical tank 58. A suction filter 63 is provided at the one end of the chemical conduit 64. The other end of the chemical conduit 64 is connected to a disinfectant solution nozzle 23. The chemical pump 65 that is constituted by a high-pressure self-priming pump for lifting the disinfectant solution from the chemical tank 58 to the cleaning/disinfecting tank 4 is interposed at a position partway along the chemical conduit 64.

In this connection, as described above, for example, two ultrasound transducers 52 and a heater 53 are arranged below the bottom surface of the cleaning/disinfecting tank 4. Further, in order to adjust the temperature of the heater 53, a temperature detection sensor 53a is provided at approximately the center of the bottom surface of the cleaning/disinfecting tank 4.

The heater 53 is used to heat the disinfectant solution that is stored in the cleaning/disinfecting tank 4 and that circulates within the apparatus to a predetermined temperature. The disinfectant solution has a proper temperature at which its disinfection effect can be expected the most. The disinfectant solution heated to the predetermined temperature that is the proper temperature by the heater 53 can effectively disinfect an endoscope and the respective conduits in the apparatus body 2.

Further, the temperature detection sensor 53a detects the liquid temperature of the disinfectant solution which is stored in the cleaning/disinfecting tank 4 and circulates in the apparatus, and transmits the detection result to the control portion 70. The control portion 70 performs control that drives and stops the heater 53 so as to keep the disinfectant solution at the predetermined temperature on the basis of the detection result from the temperature detection sensor 53a.

A power supply 71 which is supplied with electric power from an external AC receptacle, and the control portion 70 which is electrically connected to the power supply 71 are provided inside the endoscope cleaning/disinfecting apparatus 1. The control portion 70 is supplied with various signals from the main operation panel 25 and the sub operation panel 13, and performs drive control of each of the above described pumps and electromagnetic valves and the like.

In particular, the control portion 70 includes a water supply conduit disinfection program that, with respect to at least the inside of the water supply conduit 9, performs known draining, disinfecting, and rinsing through the circulation conduit 20 and the channel conduit 21 and also, with respect to at least either of tap water and a disinfectant solution inside the cleaning/disinfecting tank 4, executes a process to either recover the tap water or the disinfectant solution into the chemical tank 58 through the chemical recovery conduit 61 or drain the tap water or the disinfectant solution from an external drain outlet through the drainage conduit 59. The control portion 70 performs known driving control with respect to each valve and each pump in accordance with the water supply conduit disinfection program.

Further, the control portion 70 also includes an all conduits disinfection program that disinfects the inside of all of the conduits in the endoscope cleaning/disinfecting apparatus 1, and an endoscope cleaning/disinfecting program that cleans and disinfects endoscope conduits of an endoscope that is connected to the port 33 via a tube.

What is claimed is:

1. A chemical bottle for supplying a chemical to an endoscope cleaning/disinfecting apparatus, the endoscope cleaning/disinfecting apparatus having a limit switch, the chemical bottle comprising:

a storing section that stores the chemical and that includes an upper surface, a bottom surface facing the upper surface, a first side face that connects the upper surface and the bottom surface, and a second side face that connects the upper surface and the bottom surface and that faces the first side face;

an opening that is provided in the upper surface and whose center is disposed further to a side of the second side face than a center of the upper surface;

a concave portion that is formed in the first side face, the concave portion causing the limit switch to be closed by the upper surface and to be opened in the concave portion when the chemical bottle is moved from the upper surface towards the bottom surface; and a convex portion formed by a surface of the concave portion on a side close to the upper surface, the convex portion having a weaker mechanical strength than another area of the first side face;

wherein:

the convex portion is irreversibly deformed or broken from the bottom surface side towards the upper surface side by the limit switch when the limit switch moves in the concave portion toward the upper surface side and contacts the surface of the convex portion.

2. The chemical bottle for an endoscope cleaning/disinfecting apparatus according to claim 1, wherein the concave portion is provided in an adapter that is detachable with respect to the first side face.

* * * * *